United States Patent
Vermiglio et al.

(10) Patent No.: US 10,168,409 B2
(45) Date of Patent: Jan. 1, 2019

(54) UNIVERSAL PHANTOM STRUCTURE FOR QUALITY INSPECTIONS BOTH ON COMPUTERIZED TOMOGRAPHY AND ON MAGNETIC RESONANCE TOMOGRAPHY

(71) Applicant: IRCCS CENTRO NEUROLESI "BONINO-PULEJO", Messina (IT)

(72) Inventors: Giuseppe Vermiglio, Messina (IT); Giuseppe Acri, Dipignano (IT); Barbara Testagrossa, Messina (IT); Placido Bramanti, Messina (IT); Alessia Bramanti, Messina (IT)

(73) Assignee: I.R.C.C.S. CENTRO NEUROLESI "BONINO-PULEJO", Messina (IT)

( * ) Notice: Subject to any disclaimer, the term of this patent is extended or adjusted under 35 U.S.C. 154(b) by 397 days.

(21) Appl. No.: 15/106,387

(22) PCT Filed: Dec. 22, 2014

(86) PCT No.: PCT/IB2014/067215
§ 371 (c)(1),
(2) Date: Jun. 20, 2016

(87) PCT Pub. No.: WO2015/092776
PCT Pub. Date: Jun. 25, 2015

(65) Prior Publication Data
US 2016/0327625 A1    Nov. 10, 2016

(30) Foreign Application Priority Data

Dec. 20, 2013  (IT) .............................. RM2013A0701

(51) Int. Cl.
*A61B 5/055*    (2006.01)
*A61B 6/00*     (2006.01)
(Continued)

(52) U.S. Cl.
CPC .............. *G01R 33/58* (2013.01); *A61B 6/032* (2013.01); *A61B 6/583* (2013.01); *A61B 5/055* (2013.01)

(58) Field of Classification Search
None
See application file for complete search history.

(56) References Cited

U.S. PATENT DOCUMENTS 4,551,678 A * 11/1985 Morgan ................. G01R 33/58
                                                    324/300
6,231,231 B1 * 5/2001 Farrokhnia ............ A61B 6/583
                                                    378/204
(Continued)

FOREIGN PATENT DOCUMENTS

EP         1062912 A1    12/2000

OTHER PUBLICATIONS

International Search Report for PCT/IB2014/057215 dated Apr. 9, 2015 (2 pages).
(Continued)

*Primary Examiner* — Dixomara Vargas
*Assistant Examiner* — Douglas X Rodriguez
(74) *Attorney, Agent, or Firm* — Abelman, Frayne & Schwab

(57) ABSTRACT

The present invention relates to a phantom for periodical measurements of parameters allowing to ensure that performance of equipment for computed tomography and/or magnetic resonance tomography are compliant to established acceptability criteria, that is performance are constant in time. The main characteristic of such phantom is that the same phantom may be used for measurements of different physical parameters and for different machines, even of different type, such as machines for CT and/or MRT. The universal phantom described is made of a rectangular par-
(Continued)

allelepiped in PMMA made of different sections that may be filled with an appropriate liquid and/or contain different inserts according to the measurements to be performed, such as for example noise and uniformity, CT number linearity, high contrast spatial resolution, low contrast spatial resolution, layer thickness, etc.

11 Claims, 3 Drawing Sheets

(51) Int. Cl.
*A61B 6/03* (2006.01)
*G01R 33/58* (2006.01)

(56) References Cited

U.S. PATENT DOCUMENTS

| | | | |
|---|---|---|---|
| 2003/0086535 A1 | 5/2003 | Teppaz et al. | |
| 2005/0259793 A1* | 11/2005 | Yeo | A61N 5/1048 378/182 |
| 2008/0261009 A1* | 10/2008 | Kawabata | A61B 8/00 428/217 |
| 2008/0273654 A1* | 11/2008 | Rappoport | A61B 6/037 378/18 |
| 2015/0346351 A1* | 12/2015 | Koo | A61B 6/032 250/475.2 |
| 2017/0347987 A1* | 12/2017 | Hong | A61B 6/00 |

OTHER PUBLICATIONS

G. Acri, et al., "Slice-thickness evaluation in CT and MRIP: an alternative computerised procedure; Determinazione dello spessore dello strato in TC e RM: una procedura computerizzata alternativa," La Radiologia Medica ; Official Journal of the Italian Society of Medical Radiology, vol. 117, No. 3, pp. 507-518 (Jan. 7, 2012).

* cited by examiner

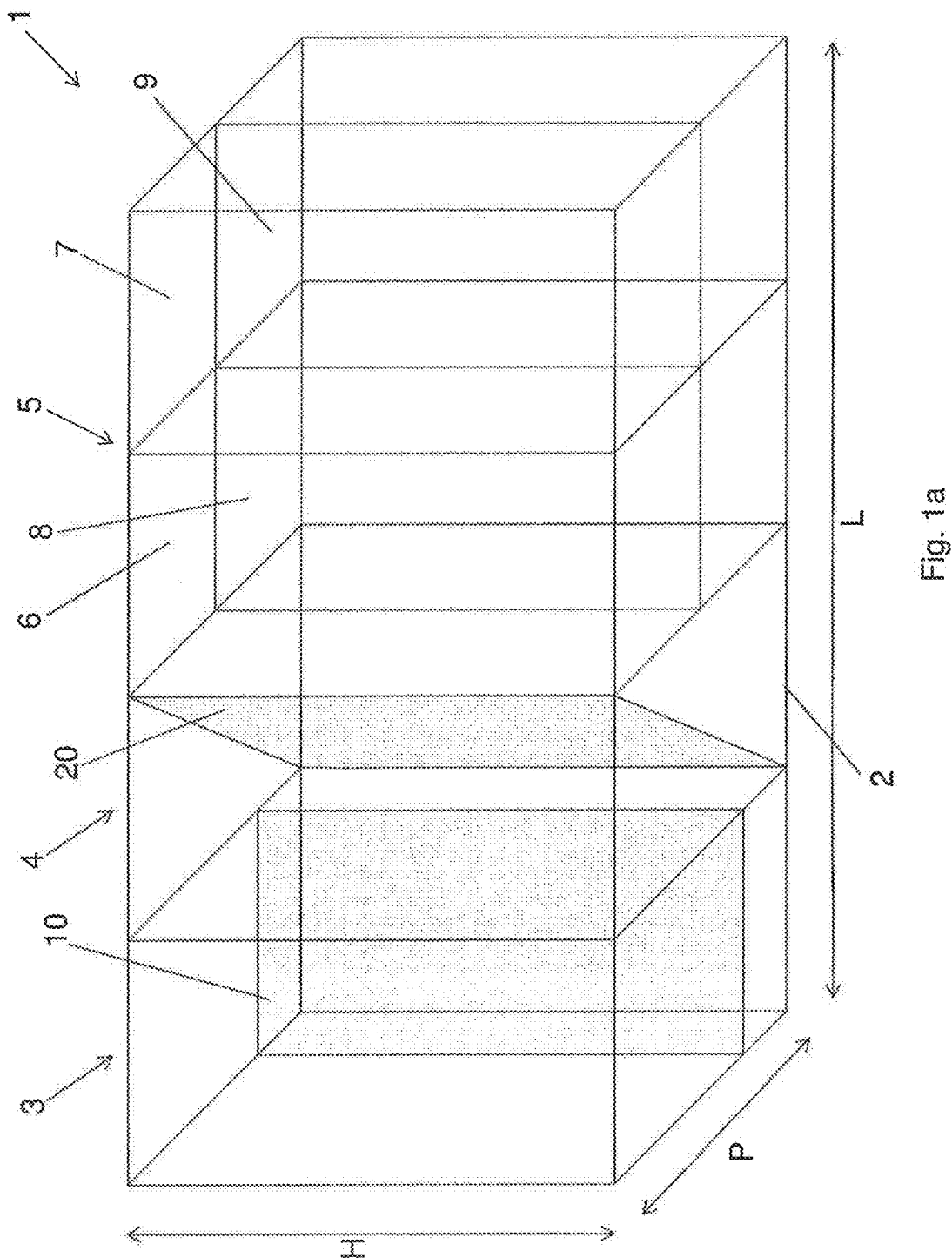

UNIVERSAL PHANTOM STRUCTURE FOR QUALITY INSPECTIONS BOTH ON COMPUTERIZED TOMOGRAPHY AND ON MAGNETIC RESONANCE TOMOGRAPHY

RELATED APPLICATIONS

This application is a national phase of International Application No. PCT/IB2014/067215 filed Dec. 22, 2014, and claims priority Italian Patent Application No. RM2013A000701 filed Dec. 20, 2013, both incorporated by reference in their entirety.

FIELD OF INVENTION

The present invention relates to a universal phantom suitable for carrying out quality inspections which can be used both on Computerized Tomography (CT) and on Magnetic Resonance Tomography (MRT) indifferently.

PRIOR ART

The object of an important category of instrumental diagnostic equipment is to produce images able to provide information as precise and accurate as possible. In particular, Computerized Tomography (CT) and Magnetic Resonance Tomography (MRT) are among the most sophisticated imaging techniques, as well as among the currently most used practices in the diagnostic activity.

The above techniques are based on high resolution images acquisition, whose quality must persist in time; for this reason, it is necessary to start adequate procedures of Quality Assurance on the instruments producing them.

Such procedures include carrying out periodic tests, aiming at identifying possible degradations on image quality, which would result in a lower capacity of correctly identifying and interpreting pathological findings, with consequent reduction of the whole diagnostic accuracy and confidence.

These tests are defined as Quality Inspections and consist in a set of tests performed in order to determine the level of reproducibility and accuracy of the diagnostic equipment performance with respect to an appropriately defined reference, provided that any imperfections or degradations of the equipment fine tuning could influence the correct diagnostic path.

In this connection, it should be noted that image quality deterioration, being a slow and progressive event, is not generally perceived by an operator that works continuously with the same equipment, needing therefore technical instruments for evaluation able to provide objective and reproducible physical parameters of measurement describing the level of performance of the radiological equipment producing diagnostic image.

Quality Inspections, such as maintenance, are recommended both by diagnostic equipment manufacturers and by Medical Physics organizations, both international and national, as well as provided by current legislation in Italy, as it is the case for MRT equipment, object of Presidential Decree no. 542/94 and for X-ray sources and machines, ruled by Legislative Decree 187/00 that provide that such controls are periodically carried out by experts with adequate qualification, degree and professional curriculum.

In order to proceed with the necessary verifications, for the quantification of surveys to be performed and the subsequent comparison of data obtained with reference values, it is necessary, however, to have specific equipment, consisting in suitable devices referred to as "phantoms", having various form and composition, constructed so as to provide a predetermined image with constant reference elements. From such particular images, one should infer the level of parameter of performance under examination.

Various types of phantoms for acquiring test images to be analyzed and processed are commercially available, mainly dedicated to the specific equipment to be tested.

Therefore, the evaluation of a number of parameters needs phantoms specifically dedicated to the equipment under examination and, in many cases, for a complete evaluation on the same equipment, it is necessary to use more than one phantom. Most often, the same manufacturer companies provide the phantoms together with the diagnostic equipment, which are therefore dedicated thereto, with the aim of being able of testing, first during acceptance, then during consistency, the relative functioning, with reference to dedicated protocols, often developed by the same companies for each machine and usually directly managed by the equipment software. Therefore, each machine has its own specific data acquisition and processing protocol, so that more often the person dedicated to measurements performing, that is the Medical Physics expert, has to use many and different types of phantoms, each of which has a dedicated measurements protocol to which one can refer.

In order to try to avoid some of the above-mentioned problems, the document XP035043505 describes a phantom which can be used both for Computerized Tomography equipment and for Magnetic Resonance Tomography equipment. Such a phantom is made of a single section divided into two compartments by a first diagonal partition and in particular it is used for the evaluation of a parameter, that is the "layer thickness". The phantom described in this document is not able to provide the evaluation of multiple parameters that should be instead evaluated to perform a more complete quality inspection of the equipment. Therefore, for evaluating parameters that can not be evaluated with such a phantom, it is necessary to use other phantoms that, as previously described, are usually specific for each equipment of a particular manufacturing company, with the above-described drawbacks. In addition, this results in considerable costs and does not make homogeneous the measurements performed for each equipment. Specifically, it is not easy or it is even impossible to compare equipment performance of different manufacturing companies.

Therefore, a single phantom would be useful that may be used to perform as much physical parameters measurements as possible, irrespective of the machine used.

SUMMARY OF THE INVENTION

Primary object of the present invention is to provide a single phantom that is suitable to perform quality inspections both on Computerized Tomography (CT) and on Magnetic Resonance Tomography (MRT), in particular able to be used to perform the evaluation of a plurality of parameters for quality inspection.

Another object of the invention is to provide a phantom which is structurally simple and cost-effective to manufacture.

Such an object is achieved by implementing a universal phantom structure for acquiring test images that, in accordance with claim 1, comprises a parallelepiped-shaped container divided by means of internal walls into sections which can be filled at least in part with a fluid according to the type of equipment to be subjected to quality inspection, said sections comprising a first parallelepiped-shaped section divided into two first compartments by a first partition, said first compartments having a mutually different volume;

a second parallelepiped-shaped section, diagonally divided into at least two second compartments by at least one second partition, so that said at least two second compartments are two triangular prisms;

and a third parallelepiped-shaped section, divided into four third compartments by two mutually transversal third partitions.

Advantageously, it is possible to provide a complete quality inspection of a CT or MRT equipment by means of the phantom of the present invention. In particular, substantially all the essential parameters that should be evaluated to obtain a complete quality inspection may be evaluated using only the phantom of the present invention. In particular, the parameters measurable with the phantom of the present invention are listed in table 1 given in this application. In this way, a more cost-effective technical solution is provided with respect to conventional quality inspections techniques. In addition, it is possible to compare the technical performance of equipment of different manufacturing companies. A further advantage is that, by using the phantom of the present invention, operators dedicated to quality inspection may perform quality inspection using a single measurement protocol for a single phantom, so it is not necessary that they are trained for using more than one measurement protocols, one for each phantom and equipment thereof.

Advantageously, the container is made of Polymethylmethacrylate (PMMA), a material which is comparable to equivalent tissue.

Advantageously, the different sections of the phantom are used, each filled at least in part with an appropriate fluid and/or filled with suitable solid inserts, for measurement of some specific physical parameters characteristic of the equipment to be subjected to quality inspection.

The dependent claims describe preferred embodiments of the invention.

BRIEF DESCRIPTION OF THE FIGURES

Further features and advantages of the invention will appear more clearly from the detailed description of a preferred but non-exclusive embodiment of a universal phantom, shown by way of a non-limiting example with the aid of the accompanying drawing tables, in which:

FIG. 1a shows a perspective view of a phantom according to the invention;

FIG. 1b shows a top view of the phantom of FIG. 1a;

FIG. 2b shows a side view of the insert of FIG. 2a;

The same reference numerals in the figures identify the same elements or components.

DETAILED DESCRIPTION OF A PREFERRED EMBODIMENT OF THE INVENTION

With the aim of identifying some procedural paths as much homogeneous as possible for the different types of equipment commercially available, thereby releasing them from what is provided for by manufacturing companies and with the aim of allowing an easier comparison of performance, both over time and among them, irrespective of any features of the person performing them, thus homogenizing methods and instruments for performing quality inspections of radiological nature, a single phantom has been developed and made which is of easy use and with extremely contained costs with respect to the various examples commercially available, to be used on CT and MRT equipment indifferently. Such a phantom has the property that it can be used for measurement of more significant parameters to determine image quality obtained both with CT and MRT tomography equipment, adequately choosing the chemical composition of the filling liquid in conjunction with respect to the specific equipment to be subjected to examination. In the following Table 1, the more significant parameters are reported, identified as such by international (AAPM-NEMA) and national (AIFB-ANPEQ-INAIL ex IspesI area) scientific associations, as well as the manufacturing companies themselves and by authors of important works present in scientific literature, through the determination of which it is possible to evaluate image quality both of CT and MRT tomography equipment, also specifying whether the relative parameter may be determined or not with the phantom of the present invention.

TABLE 1

| CT | Phantom of the Invention | MRT | Phantom of the Invention |
|---|---|---|---|
| CT numbers noise | Yes | Signal/noise ratio | Yes |
| CT numbers uniformity | Yes | Uniformity | Yes |
| Spatial resolution | Yes | Spatial resolution | Yes |
| Layer thickness | Yes | Layer thickness | Yes |
| Pixel dimension | | Precision of $T_1$ and $T_2$ | Yes |
| Contrast scale | Yes | Resonance frequency | Yes |
| Low contrast resolution | Yes | Slice warp | Yes |
| Average CT number value | Yes | Accuracy of $T_1$ and $T_2$ | Yes |
| CT number linearity | Yes | Position of the layer | Yes |
| Position of the layer | Yes | Separation among layers | Yes |
| Separation among layers | Yes | Artifacts/Ghosts | Yes |
| Accuracy of laser centering device | | Contrast/noise ratio | Yes |
| CTDI | | Accuracy of laser centering device | |
| DLP | | Geometric distortion | Yes |
| Bed positioning | | | |

Such parameters and their meaning in computed tomography and/or in magnetic resonance tomography are known by the skilled in the art.

From analysis of Table 1 it is clear that, using the phantom of the invention, it is possible to determine most of the parameters used to qualify and quantify the level of diagnostic performance of a CT/MRT tomography equipment and, among these, the more significant parameters requested, among others, by IspesI guidelines.

Figure 1B:
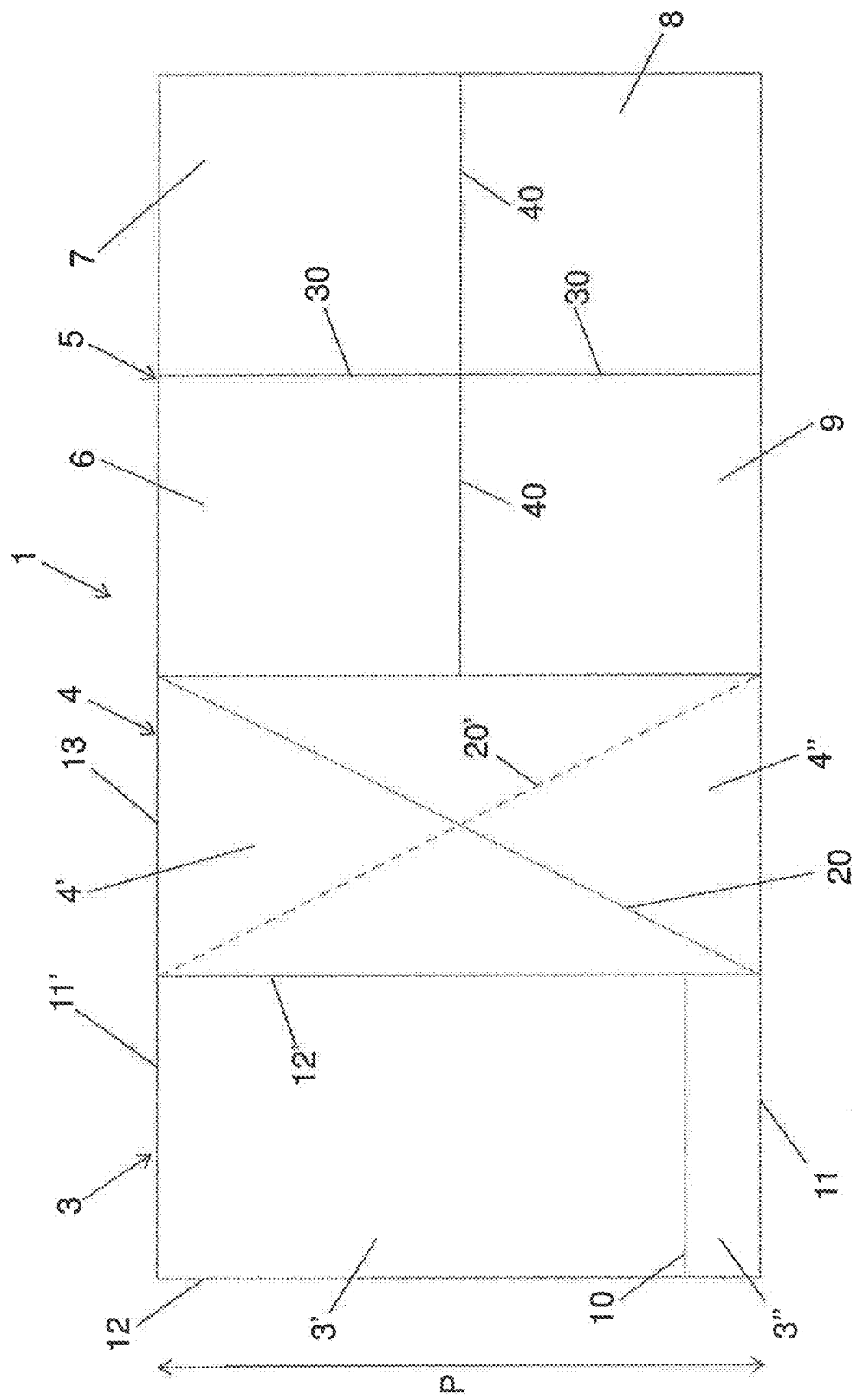

A preferred embodiment of the phantom object of the present invention is shown in FIGS. 1a and 1b. Such phantom, globally indicated with reference numeral 1, allows the performance of quality inspections both in CT and in MRT, choosing in a suitable way the chemical composition of the filling liquid of some of its parts, with respect to the specific equipment subjected to examination.

The choice of the filling liquid can be made in a known way, according to the equipment to be checked and the particular parameters to be evaluated.

The phantom 1 has preferably a rectangular parallelepiped-shape. Preferably, but not necessarily, the longitudinal extension L of base 2 of the phantom is equal to double the depth P and height H of the phantom itself. By way of a non-limiting example, a phantom variation may have the following dimensions H×W×D: 16 cm×32 cm×16 cm. In any case, the phantom of the invention results particularly compact and easy to transport or handle with respect to the phantoms currently used. Advantageously, its volume can range from 6 to 10 dm$^3$, preferably from 7 to 9 dm$^3$.

Advantageously, the phantom 1 is made of Polymethylmethacrylate (PMMA), a material which is comparable to equivalent tissue.

The phantom of the invention is advantageously divided into different sections. In the top view of FIG. 1b it is possible to better distinguish the above-mentioned sections.

A first section 3 of phantom 1, also having a rectangular parallelepiped-shape, is advantageously divided into two compartments 3', 3", separated by a partition 10, perpendicular to the bottom and two opposite first side walls 12, 12' of section 3 and therefore parallel to the two opposite second side walls 11, 11'. Partition 10, having a thickness equal to or less than 1 mm and made for example of PMMA or other suitable material, is positioned near a wall 11 of the two second side walls. Advantageously, the distance of partition 10 from the side wall 11 is equal to about ¼÷⅕ of the depth P of phantom 1, so as to allow an easy measurement on the acquired image, using the Line Profile Tool, a tool known to the skilled in the art. By way of example, this distance can range from about 2 cm to 4 cm. Again by way of example, the first section 3 may have the following dimensions H×W×D: 16 cm×8 cm×16 cm.

The side walls 12, 12' are longer than the side walls 11, 11'. The internal side wall 12' separates the first section 3 from a second section 4 of the phantom adjacent thereto.

Such a section 3 may be used to perform evaluations of uniformity (both in CT and MRT), S/N ratio (both in CT and MRT), spatial resolution (both in CT and MRT), artifacts/ghosts and resonance frequency (in MRT only). To perform the above-mentioned evaluations (quality inspections), compartments 3' and 3" are filled up to ¾ of volume, in order to distinguish, within the universal phantom, the zone filled with the dedicated liquid from the air containing zone, always within section 3.

Below, although known by the skilled in the art, we report in brief a short explanation regarding the above-mentioned parameters evaluable by means of section 3 of the phantom of the invention.

Uniformity: in CT, uniformity is the consistency of CT numbers of the image of an homogeneous material through the exam field. The CT number, expressed in Hounsfield units, HU, is an adimensional value proportional to tissue density. HUs refer to water density that, for convention, is equal to 0 since, as it is well known, the human body is composed for more than 70% of water. Above and below such value the densities of different tissues of living matter occur. In MRT, image uniformity is relative to the ability of the MRT system to produce a constant response signal on the mapped volume when the object whose the image is acquired has homogeneous MRT characteristics.

S/N ratio (Signal/Noise): in CT, noise is defined as the variation of CT numbers with respect to the average value in a defined area, referred to as region of interest (ROI), at the center of the image of the uniform substance. The entity of the noise is evaluated by means of standard deviation, provided by the console, of CT numbers. In MRT, noise is defined as the variation of signal in an homogeneous region. On a single image small ROIs are selected, but with statistics above 100 pixels, on which the signal S is evaluated as average value of signal distribution in ROI and noise N as standard deviation of the same distribution. The protocol suggests to take five regions positioned one at the center and the other four in orthogonal positions to each other in more peripheral regions, but avoiding the edge zone to evaluate the homogeneity of S/N.

Spatial resolution: in CT, spatial resolution is the ability to distinguish between different objects in the image; when the difference of attenuation between objects and background is high compared to noise, it may be evaluated by means of the response function to a PSF pulse, Point Spread Function, that is the response of the system to a precise stress, that is to a single pixel. In MRT, spatial resolution is the ability to distinguish between different objects in the image; it may be evaluated by means of the response function to a PSF pulse.

Artifacts/Ghosts: in MRT, they consist in the presence of a signal significantly different from background in regions of the image in which the Signal Producing Volume does not exist.

Resonance frequency: in MRT, the software returns the resonance frequency within the selected ROI. Such value is compared to the nominal value.

A second section 4 of phantom 1, also having a rectangular parallelepiped shape, and adjacent to said first section 3, is advantageously divided in at least two compartments 4', 4", separated by a partition 20, substantially perpendicular to the background of section 4 and arranged diagonally within section 4 so as to form two equal triangular prisms, having a base formed by a right triangle, that define the above-mentioned compartments 4', 4". For the evaluation of various parameters, only one of the two compartments 4', 4" is filled with a suitable liquid, which will be specific in relation to the equipment subjected to examination. Partition 20 has a thickness equal to or less than 1 mm and it is made for example of PMMA or other suitable material with similar attenuation properties.

Advantageously, the second section 4 has the same volume (dimensions) of the first section 3, for example H×W×D: 16 cm×8 cm×16 cm.

The second section 4 may be used for performing evaluations of position of the layer (both in CT and MRT), layer thickness (both in CT and MRT), layer separation (both in CT and MRT), Slice Warp (in MRT only). To perform the above-mentioned evaluations (quality inspections) the compartment 4' is filled with a suitable filling liquid, while the compartment 4" is full of air, or vice versa, or the two compartments 4', 4" are filled with two fluids having different densities. The second section 4 is thus able to reproduce the ramp and wedge behavior.

Below, although known by the skilled in the art, we report in brief a short explanation regarding the above-mentioned parameters evaluable by means of section 4 of the phantom of the invention.

Position of the layer: in CT and MRT, the control on the position of the layer allows to exactly determine the position of the acquired layer, the latter being set using the centering systems available.

Layer thickness: in CT and MRT, layer thickness is determined by full width at half maximum (FWHM) of the profile of the irradiated slice, by means of the Line Profile Tool (known by the skilled in the art), multiplied by the tangent of the angle, obtained as the ratio between catheti 13 and 12'.

Layer separation: in CT and MRT, the test consists in the verification of the distance set among layers. The evaluation provides the graphic overlapping of the profiles of the ramp of each acquired layer and the calculation of the central value of each peak.

Slice Warp: in MRT, the test consists in the qualitative verification of the perfect horizontality of the acquired layer.

In an alternative variant, in the second section 4 another partition 20' may be provided, arranged diagonally within section 4 transversally to the other partition 20, so as to divide section 4 in four triangular prisms, equal in pairs, having a base formed by an isosceles triangle and defining four compartments. In this case, to perform the above-mentioned evaluations (quality inspections), the compartments are filled exactly in the same way as described above, but in this case the system is able to reproduce the typical behaviour of the double wedge, known by the skilled in the art.

A third section 5 of phantom 1, preferably having a cubic shape and adjacent to said second section 4, is advantageously divided into four compartments 6, 7, 8, 9. In a preferred variation, compartments 6, 7, 8, 9 having a parallelepiped shape are equal to each other and are obtained dividing the volume of the cube of the third section 5 by means of two partitions 30, 40 equal and orthogonal to each other. Partitions 30, 40 define together a Greek cross shape in the top view of the phantom (FIG. 1b). Also partitions 30, 40 have a thickness equal to or less than 1 mm and are made for example of PMMA or other suitable material with similar attenuation properties.

Advantageously, the third section 5 has equal depth P and height H than sections 3 and 4, but it exhibits a longitudinal extension equal to about double the longitudinal extension of each of the sections 3 and 4. By way of example, the third section 5 may have the following dimensions H×W×D: 16 cm×16 cm×16 cm, and the compartments 6, 7, 8, 9 may have the following dimensions H×W×D: 16 cm×8 cm×8 cm.

The four compartments of third section 5 may be used to perform evaluations of the following eight characteristic parameters useful for carrying out quality inspections: average CT number value (in CT), CT number linearity (in CT), contrast scale (in CT), low contrast resolution (in CT), precision of the relaxation times T1 and T2 (in MRT), accuracy of relaxation times T1 and T2 (in MRT), contrast/noise ratio (in MRT) and geometric distortion (in MRT). Four of these parameters are relative to computed tomography; the other four are relative to magnetic resonance tomography.

Below, although known by the skilled in the art, we report in brief a short explanation regarding the above-mentioned parameters evaluable by means of section 5 of the phantom of the invention:

Average CT number value: the average CT number value representing the average attenuation associated to each elementary area of the CT image shall be compared to the reference value.

CT Number linearity and contrast scale: in CT, CT number linearity consists in the evaluation of the linear correspondence between CT number and physical (or electronic) density or the coefficient of attenuation. A synthetic index of linearity consists of the contrast scale defined as the right line slope representing the coefficient of linear attenuation in function of CT numbers.

Low contrast resolution: in CT is the ability to highlight tissues having small differences of electronic density.

Precision of the relaxation times T1 and T2: in MRT the precision of evaluation of the two relaxation times spin-lattice and spin-spin is defined as the variation of evaluation in a repeated series of measurements under identical conditions.

Accuracy of the relaxation times T1 and T2: in MRT the accuracy of evaluation of the two relaxation times spin-lattice and spin-spin is defined as the variation of evaluation of such parameters compared to standard reference values.

Contrast/noise ratio: in MRT it represents the ability of the system to distinguish between regions having different relaxation characteristics and proton density compared to noise.

Geometric distortion: in MRT, geometric distortion is related to the ability of the system to reproduce the dimensions of an object.

To perform the above-mentioned evaluations (quality inspections), compartments 6, 7, 8 and 9 are filled in part with a suitable filling liquid, according to the equipment to be examined; in addition, respective mobile solid inserts corresponding to a different parameter to evaluate are inserted therein.

Figure 3:
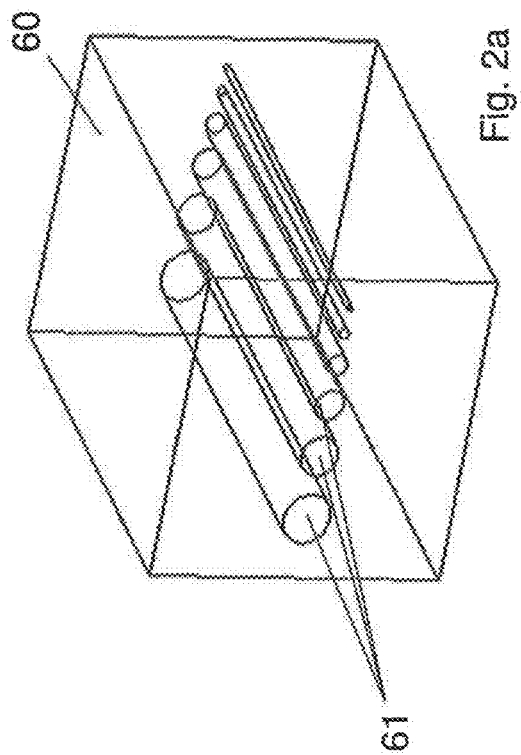
FIG. 3 shows a second type of insert for performing Quality Inspections in Computerized Tomography equipment.

FIG. 3 shows an example of a first type of inserts 50 for performing quality inspections on CT equipment. Two cubic-shaped inserts 50, having for example dimensions of 6 cm×6 cm×6 cm, made of materials which are different from each other, for example PMMA and Teflon, may be used to verify the average CT number value, as well as to evaluate the linearity of the same. Each insert 50 is inserted within a respective cubic compartment of section 5, for example having dimensions of 8 cm×8 cm×8 cm, filled in part with a predetermined liquid.

Figure 2A:
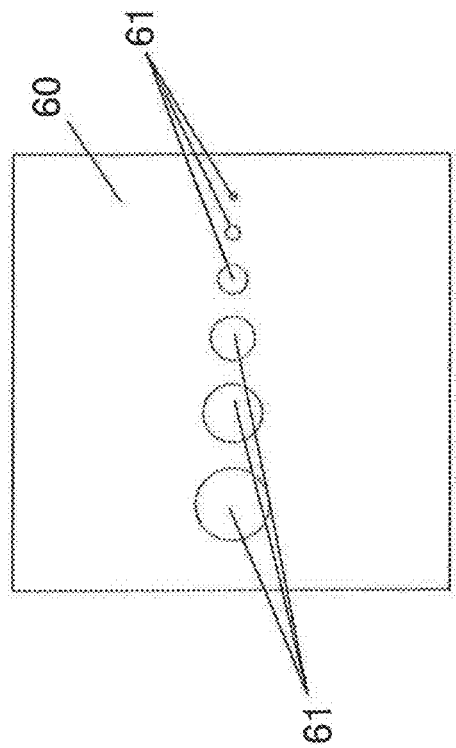
FIG. 2a shows a perspective view of a first type of insert for performing Quality Inspections in Computerized Tomography equipment.
Figure 2B:
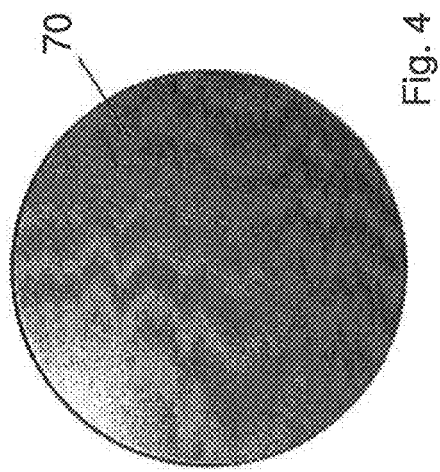

FIGS. 2a and 2b show an example of a second type of inserts 60 for performing quality inspections on CT equipment.

Insert 60 is also a cube, made for example of PMMA and having for example dimensions of 6 cm×6 cm×6 cm. Advantageously, the cubic insert 60 exhibits inside a series of cylindrical holes 61 arranged parallel to each other, with their own longitudinal axis arranged along one same centerline plane of the cube and passing through the cube from a wall to the opposite one; said cylindrical holes 61 having a decreasing diameter going from one part to the other of the cube. The visualization of the above-mentioned cylindrical holes 61 allows to obtain information regarding the contrast scale of the tomography equipment subjected to quality inspection.

By way of example, six cylindrical holes 61 may be provided having, in sequence, a decreasing diameter equal to 10 mm, 8 mm, 6 mm, 4 mm, 2 mm, 1 mm, respectively (FIG. 2b).

Inserts 60 may be used for verifying contrast scale and low contrast resolution in CT.

Each insert 60 is inserted within a respective compartment of section 5, filled in part with a predetermined liquid.

Figure 4:
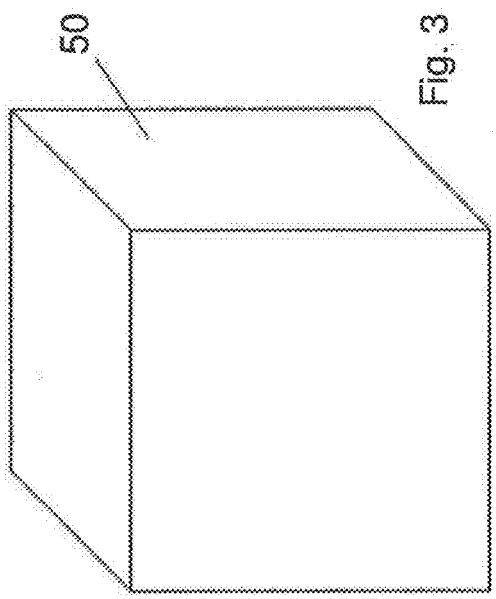
FIG. 4 shows a third type of insert for performing Quality Inspections in Magnetic Resonance Tomography equipment.

Instead, FIG. 4 shows an example of a third type of inserts 70 for performing quality inspections on MRT equipment. A plurality of spherical-shaped inserts 70, having equal dimensions, for example having a radius of about 2-4 cm, made of PMMA, are filled with different liquids and positioned inside the previously identified compartments 6, 7, 8, 9, in turn previously filled with appropriate liquid. These inserts 70 allow to evaluate the precision of the relaxation times T1 and T2, the accuracy of said relaxation times T1 and T2, contrast/noise ratio and geometric distortion, respectively.

Therefore, the phantom of the present invention, having a compact, easy and cost-effective structure, allows to evaluate, by means of insertion of adequate liquids and/or inserts, substantially all the main parameters useful for determining image quality obtained both with CT and MRT tomography equipment.

The preliminary results obtained comparing the universal phantom, object of the present invention and the phantoms currently used for performing Quality inspections in CT and in MRT have shown a discrepancy below 3%.

The invention claimed is:

1. A phantom structure configured to acquire test images and to perform quality inspection on CT or MRT equipment, said phantom structure comprising:
   a parallelepiped-shaped container divided into sections by internal walls, said sections including:
      a first parallelepiped-shaped section divided into two first compartments by a first partition, said two first compartments each having a mutually different volume;
      a second parallelepiped-shaped section diagonally divided into at least two second compartments by at least one second partition so that said at least two second compartments are triangular prisms; and
      a third parallelepiped-shaped section divided into four third compartments by two mutually transversal third partitions.

2. The phantom structure according to claim 1, wherein the first section, the second section and the third section are arranged in sequence along a longitudinal axis of the container.

3. The phantom structure according to claim 1 wherein the parallelepiped-shaped container is rectangular, the first section is rectangular parallelepiped-shaped, the second section is rectangular parallelepiped-shaped and the third section is cube-shaped.

4. The phantom structure according to claim 3, wherein said first section has dimensions which are equal to dimensions of the second section and wherein the third section has a depth (D) and a height (H) equal to those of said first and second sections and said third section further comprises a longitudinal extension equal to double the longitudinal extension of either of first section or second section.

5. The phantom structure according to claim 1, further comprising an additional second partition in said second section, said additional second partition being arranged diagonally inside the second section and transversally to said second partition so as to divide the second section into four triangular prisms (equal in pairs) of two equal parts defining four second compartments.

6. The phantom structure according to claim 1, wherein the first partition is perpendicular to the bottom of the container and to two first opposite side walls of said first section and is parallel to two second opposite side walls of said first section.

7. The phantom structure according to claim 6, wherein said first partition lies near a wall of said two second opposite side walls.

8. The phantom structure of claim 7, wherein a distance of said first partition from said wall is about ¼-⅛ of said container depth.

9. The phantom structure according to claim 1, wherein said four third compartments are mutually equal, divided by two third partitions (30, 40) which are mutually equal and orthogonal.

10. The phantom structure according to claim 1, wherein the container, said first partition, said at least one second partition and said third partitions are made of polymethylmethylacrylate (PMMA).

11. The phantom structure of claim 1, wherein said container, said first partition, said at least one second partition and said third partitions are made of material having water-like attenuation properties.

* * * * *